United States Patent [19]

Nakano et al.

[11] Patent Number: 5,021,419
[45] Date of Patent: Jun. 4, 1991

[54] NOVEL PYRAZINOXIDE COMPOUND OF NF-1616-904 AND A PHARMACEUTICAL COMPOSITION CONTAINING THE SAME

[75] Inventors: Yoshimasa Nakano; Michiharu Sugawara; Setsuyoshi Uetsuki; Taketoshi Izawa; Tomoyuki Kawaguchi; Akira Wada, all of Tokushima, Japan

[73] Assignee: Otsuka Pharmaceutical Co., Ltd., Tokyo, Japan

[21] Appl. No.: 518,252

[22] Filed: May 7, 1990

Related U.S. Application Data

[63] Continuation of Ser. No. 230,829, Aug. 11, 1988, abandoned.

[30] Foreign Application Priority Data

Aug. 11, 1987 [JP] Japan .................... 62-201537

[51] Int. Cl.⁵ ............... A61K 31/495; C07D 403/06
[52] U.S. Cl. ............................ 514/253; 514/825; 544/405
[58] Field of Search ............... 514/253, 825; 544/405

[56] References Cited

FOREIGN PATENT DOCUMENTS 0181152 5/1986 European Pat. Off. .

OTHER PUBLICATIONS

Simpson et al., Journal of Laboratory and Clinical Medicine, pp. 13-30 (1987).
Laurent et al., American Journal of Physiology (1986) pp. 765-776.
Fantone et al., The American Journal of Pathology (1982) pp. 397-418 (vol. 107, No. 3).
Taber's Cyclopedic Medical Dictionary, Edited by Thomas 16 Edition, pp. 922-923, 1580-1581 (1989).
Tsuruo et al., CA 105-164596m (1986) "Characteristics of Vincristine Resistance in . . . ".
Chemical Abstracts, vol. 95, 1981, p. 738, Abstract No. 7743q.

Primary Examiner—Cecilia Shen
Attorney, Agent, or Firm—Sughrue, Mion, Zinn Macpeak & Seas

[57] ABSTRACT

A novel pyrazinoxide compound of NF-1616-904 having the formula (1),

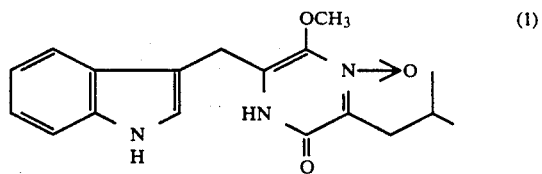

prepared by hydrolyzing the intermediate compound of NF-1616-902 which is separated from a culture broth of a microorganism belonging to the genus Thielavia.

The pyazinoxide compound of NF-1616-904 possess biological and pharmacological activities, and is useful agent for preventing and treating diseases caused by superoxide radicals ($O_2^-$), and nephritis.

8 Claims, 3 Drawing Sheets

NOVEL PYRAZINOXIDE COMPOUND OF NF-1616-904 AND A PHARMACEUTICAL COMPOSITION CONTAINING THE SAME

This is a continuation of Ser. No. 230,829, filed Aug. 11, 1988, now abandoned.

FIELD OF THE INVENTION

The present invention relates to a pyrazinoxide compound of NF-1616-904. More particularly, the invention relates to a novel pyrazinoxide compound of NF-1616-904, process for preparing said compound, and a pharmaceutical composition containing said compound as the active ingredient.

PRIOR ART

The pyrazinoxide compound of NF-1616-904 of the present invention is a novel compound which has not been known in any prior art literature.

SUMMARY OF THE INVENTION

An object of the present invention is to provide a novel pyrazinoxide compound of NF-1616-904.

Another object of the present invention is to provide a process for preparing said pyrazinoxide compound of NF-1616-904.

Further object of the present invention is to provide a pharmaceutical composition containing said pyrazinoxide compound of NF-1616-904 as the active ingredient.

DETAILED DESCRIPTION OF PREFERRED EMBODIMENTS

The above-mentioned objects of the present invention can be achieved by the novel pyrazinoxide compound of NF-1616-904 having the formula (1) as follows:

(1)

As the result of an extensive research work made by the present inventors, it was found the fact that a novel substance, having the specific biological activities, can be produced by culturing a microorganism which was isolated from a soil sampled in Iriomote-jima, Okinawa-ken, Japan. Then, the present invention had been successfully completed by finding the fact that the novel pyrazinoxide compound of NF-1616-904 can be produced by hydrolyzing the above-mentioned novel substance as the intermediate.

Preparations of the novel substance to be used as the intermediate compound and the novel pyrazinoxide compound of NF-1616-904 of the present invention are explained in detail as follows.

The intermediate compound to be used in preparation of the desired pyrazinoxide compound of NF-1616-904 of the present invention can be produced by culturing a microorganism.

As to specific example of strain of the microorganism for use in producing the intermediate compound, the strain belonging to the genus Thielavia which was isolated from the soil sampled in Iriomotejima, Okinawa-ken, Japan, can be used. Said strain was nominated as *Thielavia minor* OFR-1561 and was deposited at the Fermentation Research Institute, Agency of Industrial Science and Technolog with the Deposit No. FERM BP-1908.

Mycological properties of said strain are shown as follows.

(a) Morphology:

According to microscopic observations, the cleistothecia are globose or subglobose, having a size of 40 to 100 μm in diameter, dark brown in color, neckedness with smooth surface. The peridia are semitransparent. The asci are 8-spored and are a wide pyriform or ovoid, and having a size of 20-25 × 11-15 μm, as well as evanescent. The ascospores are ellipsoidal, having a size of 8-11 × 6-8 μm, at first, colorless then turned to dark olive or olive brown in color. Both sides of smooth surface are peaked slightly, and a single apical germpore formed. Conidia are not observed.

(b) Growing states on various agar culture media:

Visual observations of giant colonies which were grown on various agar culture media by inoculating the strain at 37° C. for 10 days.

i) Malt extract-agar culture medium

Well grown. White cotton-like hyphae are grown with piled-up shape. Ascocarps are formed abundantly. Back side of the colonies are white or dark green in color.

ii) Potato-glucose-agar culture medium

Well grown. White cotton-like hyphae are wide. Ascocarps are formed less in number. Back side of the colonies are dark green in color.

iii) Sabouraud's agar culture medium

Well grown. White cotton-like hyphae are only observed. Formation of ascocarps are not observed. Back side of the colonies are light yellow in color.

iv) YpSs-agar culture medium

Well grown. White hyphae are dispersed out thinly on the surface. Ascocarps of grey or black in color are abundant on the surface of the colonies. Back side of the colonies are colorless.

(c) Physiological properties:

Growing temperature: 18° to 43° C.

Growing pH range: pH 3 to 10

Optimum growing temperature: 25° to 39° C.

Optimum growing pH range: pH 5 to 8

On the basis of the above-mentioned mycological properties and by the methods according to those described in an article "The Genus Thielavia" by David Malloch and R. F. Cain, in Mycologia, Vol. 65, (1973), pages 1055-1077, and in an article "Les Thielavia des sols arides: especes nouvelles et analyse generique" by Jean Mouchacca, in Bulletin Trimestriel Societe Mycologique France, Vol. 89, (1973), pages 95-311, this strain was determined as a strain belonging to the *Thielavia minor*, for the reasons that the surface of perithecium is smooth, ascopores having a size of 8-11 × 6-8 μm, with a single apical germpore, as well as it does not form condia. Finally, the strain was nominated as *Thielavia minor* OFR-1561 (FERM BP-1908).

According to the present invention, the intermediate compound for use in preparation of the desired novel pyrazinoxide compound of NF-1616-904 is produced by culturing the above-mentioned strain of *Thielavia minor* OFR-1561 or any mutants thereof belonging to the genus Thielavia, capable of producing the above-mentioned intermediate compound, in a suitable culture medium. Culturing of the above-mentioned microorganisms may be carried out by conventional method for culturing common microorganisms, and generally the methods can preferably be carried out under aerobic conditions, for example liquid culture, shaking culture, aerated agitation culture and the like.

As to the culture media which can be used for culturing the microorganisms, any culture media containing nutrients sources usable by the above-mentioned microorganisms belonging to the genus Thielavia, thus various synthetic culture media, semi-synthetic culture media, natural culture media and the like can be used. As to the carbon sources in the formulation of the culture media, glucose, sucrose, fructose, glycerin, dextrine, starch, molasses, corn steep liquor and organic acids can be used, singly or in combination thereof. As to the nitrogen sources in the formulation of the culture media, organic nitrogen cources such as, Pharmamedia peptone, meat extract, yeast extract, soybean powder, casein, amino acids, urea and the like, and inorganic nitrogen sources, such as sodium nitrate, ammonium sulfate and the like can be used, singly or in combination thereof. If necessary, sodium salts, potassium salts, magnesium salts, phosphates and other heavy metal salts may be added to the culuture media. In addition to the above, in the case that if the culture medium is foamed in certain extent, then any known anti-foaming agent can be added to the culture medium. However, such addition of the anti-foaming agent should not give any adverse effect for producing the desired intermediate compound.

The pH of the culture medium may preferably be controlled to an optimum pH range of the microorganism to be used, generally the pH is controlled to about a natural range. The growing temperature may be controlled to about temperature good for growing the microorganism, generally the temperature is kept to about 20°-40° C., preferably it may be kept to about 30° C. The culturing time is, in the case of a liquid culture, generally about 1 to 5 days.

According to the above-mentioned culture, the desired intermediate compound is produced and accumulated in the culture broth. As a matter of course, the above-mentioned various culturing conditions may suitably be changed depend on the type and characteristics of the microorganism to be used, as well as the external conditions. Thus, the optimum culturing conditions can be selected and controlled depend on the ranges of these factors.

When the desired intermediate compound produced in the culture medium is accumulated in the maximum quantity, the desired intermediate compound may be separated by methods generally employed for obtaining the fermentation products, for example salting out method such as precipitation method with ammonium sulfate, dialysis method, extraction method, various gel chromatography, ion-exchange chromotography, adsorption chromatography and the like, singly or in combination thereof in an optimum order.

More particularly, since the desired intermediate compound produced by the above-mentioned culturing process is mostly contained in the culture broth (filtrate), the mycelium of the solid portion in the culture broth is first separated by means of filtration or centrifugal separation, then the filtrate thus obtained is extracted with ethyl acetate, and the organic layer of extract containing the desired intermediate compound is concentrated, next the concentrated liquor may be subjected to purification by means of a chromatography, such as a silica gel column chromatography, Sephadex LH-20 column (manufacture by Pharmacia Fine Chemicals, Inc.) chromatography and the like. The details of purification method will be shown in Example 1 mentioned later.

The intermediate compound thus obtained is determined by its physico-chemical properties as shown in Example 1 mentioned later. The present inventors had nominated this intermediate compound as NF-1616-902. This intermediate compound of NF-1616-902 is useful as for preparing the desired pyrazinoxide compound of NF-1616-904 of the present invention and also as shown in the Pharmacological Test-1 mentioned later, the intermediate compound of NF-1616-904 per se possesses some specific biological and pharmacological activities which can be able to decrease the tolerance of cancer cells against various anti-tumor agents by using it in combination with said anti-tumor agents. Thus, the intermediate compound of NF-1616-902 is quite useful agent for the therapy of cancers.

The desired pyrazinoxide compound of NF-1616-904 of the present invention is prepared by hydrolyzing the above-mentioned intermediate compound of NF-1616-902 under conditions similar to those employed in usual hydrolysis in the presence of an alkali.

When said hydrolysis is completed, the desired pyrazinoxide compound of NF-1616-904 can easily be separated by means of usual separation and purification means, such as solvent extraction method, column chromatography method, recrystallization method and the like. More specifically, as to the separation means, for example the hydrolyzed mixture is extracted with ethyl acetate, then said extract is subjected to a column chromatography, such as by using Sephadex LH-20 colum, and the fraction obtained therefrom is crystallized from methanol to obtain the desired pyrazinoxide compound of NF-1616-904, advantageously.

Thus obtained pyrazinoxide compound of NF-1616-904 of the present invention possesses an inhibitory effect against superoxide radicals ($O_2^-$) released from the macrophage cells of guinea pig by stimulation, and also possesses an anti-albuminuria activity in Masugi nephritis. Thus, the pyrazinoxide compound of NF-1616-904 is useful agent for preventing and treating of various diseases caused by the above-mentioned superoxide radicals, for example diseases of autoimmune such as rheumatoid arthritis arteriosclerosis, ischemic heart disease, transient cerebral ischematic attack, hepatic insufficiency, renal insufficiency and the like, as well as useful agent for preventing and treating the nephritis in various clinical fields.

In using the desired pyrazinoxide compound of NF-1616-904 or the intermediate compound of NF-1616-902 as the active ingredient in the pharmaceutical compositions, each one of these compounds can be used in any form of usual pharmaceutical compositions which can be prepared by using with usual pharmaceutically acceptable cerriers. Examples of such pharmaceutically acceptable carriers are selected depending on the desired form of pharmaceutical compositions, including diluents and excipients such as fillers, diluents, binders, wetting agents, disintegrating agents, surface active agents, lubricants, etc. The pharmaceutical compositions can be selected from any desired unit form depending on the purpose of therapy, including tablets, pills, powders, liquors, suspensions, emulsions, granulars, capsules, suppositories, injection preparations (e.g., solutions, suspensions, etc.), ointments and the like.

For the purpose of to prepare tablets form composion, carriers which are widely used in this field can be applied, for example, excipients such as lactose, sucrose, sodium chloride, glucose, urea, starch, clacium carbonate, kaolin, crystalline cellulose, silicic acid, etc.; binding agents such as water, ethanol, propanol, simple syrup, glucose solutions, starch solutions, gelatin solutions, carboxylmethyl cellulose, shelac, methyl cellulose, potassium phosphate, polyvinylpyrrolidone, etc.; disintegrating agents such as dried starch, sodium alginate, agar-agar powder, laminalia powder, sodium hydrogen carbonate, calcium carbonate, esters of polyoxyethylene sorbitan fatty acids, sodium laurylsulfate, monoglyceride of stearic acid, starch, lactose, etc.; disintegration inhibitors such as sucrose, stearin, coconut butter, hydrogenated oils, etc.; absorption accelerators such as quaternary ammonium bases, sodium laurylsulfonate, etc.; wetting agents such as glycerin, starch, etc.; adsorbing agents such as starch, lactose, kaolin, bentnite, colloidal silicic acid, etc.; and lubricants such as purified talc, stearic acid salts, boric acid powder, polyethylene glycols etc. If necessary, the tablets can further be coated with usual coating materials to make them into the form of coated tablets, for example tablets coated with sugar, tablets coated with gelatin film, tablets coated with enteric coating layers, tablets coated with films or double layered tablets and multi-layered tablets.

For the purpose of to make in the form of pills, carriers which are known and widely used in this field can be also applied, for example excipients such as glucose, lactose, starch, coconut butter, hydrogenated vegetable oils, kaolin, talc, etc.; binders such as powdered gum arabic, powdered Tragacanth, gelatin and ethanol; disintegrators such as laminalia and agar-agar, etc., are included.

For the purpose of to make in the form of suppositories, carriers which are known and widely used in this field can also be applied, for example polyethylene glycols, coconut butter, higher alcohols, esters of higher alcohols, gelatin, semi-synthesized glycerides, etc., are included.

For the purpose of to make in the form of capsules, the active ingredient is admixed with the above-mentioned carriers by means of usual method, and the mixture is filled in solid gelatin capsules or in soft capsules.

For the purpose of to make in the form of injection preparations, the solutions or suspensions of the active ingredient are sterilized and are preferably isotonic to the blood. In making injection preparations in the form of solutions, emulsions and suspensions, every diluents which are commonly used in this field can also be applied, for example, water, ethyl alcohol, polyethylene glycols, propylene glycol, ethoxylated isostearyl alcohol, polyoxylated isostearyl alcohol, polyoxyethylene sorbitan fatty acid esters, etc., are included. In these instances, an adequate amount of sodium chloride, glucose, or glycerin can be added to contain in the desired preparations for the purpose of to make them isotonic. Furthermore, usual dissolving agents, buffers, analgesic agents and other agents can be added, as well as coloring agents, preservatives, perfumes, seasoning agents, sweetening agents and other medicines can also be added into the desired preparations, if necessary.

For the purpose of to make in the form of paste, cream and gel preparations, diluents such as white petrolatum, paraffin, glycerin, cellulose derivatives, polyethylene glycols, silicones, bentonite and the like may be used.

The amount of the active ingredient to be contained in the above-mentioned pharmaceutical compositions is not specifically restricted, and can be selected from a wide range, generally 1–70% by weight of the active ingredient may be contained in the whole composition.

Method for administering the pharmaceutical composition of the present invention is not specifically restricted, and the composition can be used in various forms of preparations depending upon the age, the distinction of gender, the degree of symtoms and other conditions of the patient without may restriction. For example, tablets, pills, solutions, suspensions, emulsions, granules and capsules are administered orally; injection preparations are administered intraveneously singly or in combination with usual injectable transfusions such as glucose solutions, amino acids solutions and others; and if necessary, the injection preparations are administered singly intramuscularly, intracutaneously, subcutaneously or intraperitoneally. The suppositories are administered into the rectum.

The dosage of the above-mentioned pharmaceutical compositions according to the present invention may be selected suitably depend on the method for administrations, the age of the patient, the distinction of gender, and other conditions, as well as the degree of the symptoms, and generally 0.5 to 30 mg/kg of the body weight per day of the active ingredient may be administrated, and such pharmaceutical composition is administered in 1 to 4 times a day, dividedly.

The present invention will be illustrated by showing examples of preparation of the intermediate compound of NF-1616-902, and the desired pyrazinoxide compound of NF-1616-904, and pharmacological tests of each of these compounds. However, the present invention is not restricted only to these examples.

EXAMPLE 1

Preparation of the intermediate compound of NF-1616-902

1) Culturing of *Thielavia minor* OFR-1561 (FERM BP-1908):

100 Milliliters of a culture medium consisting of 30 g/liter of starch, 5 g/liter of glucose, 5 g/liter of soybean powder, 1 g/liter of yeast extract, 1 g/liter of polypeptone, 3 g/liter of $CaCO_3$ and 0.5 g/liter of $MgSO_4$ was placed in a conical flask having 500 ml capacity.

One Pt-loopful amount of mycelium of *Thielavia minor* OFR-1561 (FERM BP-1908) strain being deposited at Fermentation Research Institute, Agency of Industrial Science and Technology, stocked on a slant agar culture was inoculated in the above-mentioned culture medium and subjected to shaking culture or rotating culture at 28° C. for 96 to 120 hours.

The above-mentioned mycelia of *Thielavia minor* OFR-1561 (FERM BP-1908) was cultivated and stored on a slant agar culture (pH 6.5) containing 4% of maltose, 1% of polypeptone and 2% of agar, for 1 week at below 30° C.

2) Purification of the intermediate compound of NF-1616-902

After finished the above-mentioned culture of *Thielavia minor* OFR-1561 (FERM BP-1908), 100 ml of filtrate was obtained from the culture broth by filtration.

The above-mentioned filtrate was extracted with ethyl acetate, and the ethyl acetate layer was concentrated, then the thus obtained concentrate was subjected to purification by means of a silica gel column chromatography (eluent:chloroform:ethyl acetate=2:1) to obtain an active fraction. Said active fraction was subjected to treatment by means of Sephadex LH-20 column manufactured by Pharmacia Fine Chemicals, Inc.), then the fractions eluted with an eluent (chloroform:methanol=1:1) were collected and concentrated to yield the desired intermediate compound of NF-1616-902.

3) Identification of the desired intermediate compound

The thus obtained intermediate compound of NF-1616-902 was physico-chemical properties as follows.

(1) Rf value of TLC (thin-layer chromatogram):

When a mixed solvent (benzene:ethyl acetate:methanol=3:1:0.2) was used as the developer, the Rf value on TLC plate (manufactured by Merck & Co., Inc.) was 0.40.

(2) Color change after mixed with 50% $H_2SO_4$: Changed to yellow in color.

(3) Solubilities in various solvents:

| Solvent | Solubility |
| --- | --- |
| Ethyl acetate | ++ (Slightly soluble) |
| Hexane | − (Insoluble) |
| Dimethyl sulfoxide | +++ (Easily soluble) |
| Chloroform | ++ (Slightly soluble) |
| Benzene | + (Hardly soluble) |
| Methanol | +++ (Easily soluble) |
| Water | − (Insoluble) |

(4) Melting point:

Not in crystal form, thus indefinite form substance, not gave clear melting point, it melts at temperature of 191° to 194° C.

(5) Mass spectrum (EI):
$M^{\oplus} = 327$ (6) FAB (fast atom bombardment) Mass spectrum:
$[M+1] = \oplus 653$
$[M+Na]^{\oplus} = 675$ (7) Ultraviolet absorption spectrum (Ethanol):

$\lambda max\ (E^{1\%}_{1\ cm})$ = 352 (233, $\epsilon$ = 15160)
287 (256, $\epsilon$ = 16680)
235 (sholder)
232 (791, $\epsilon$ = 51550)

(8) Optical rotation:
$[\alpha]_D^{26} = 775$ (c=1, $CHCl_3$)

Figure 1:
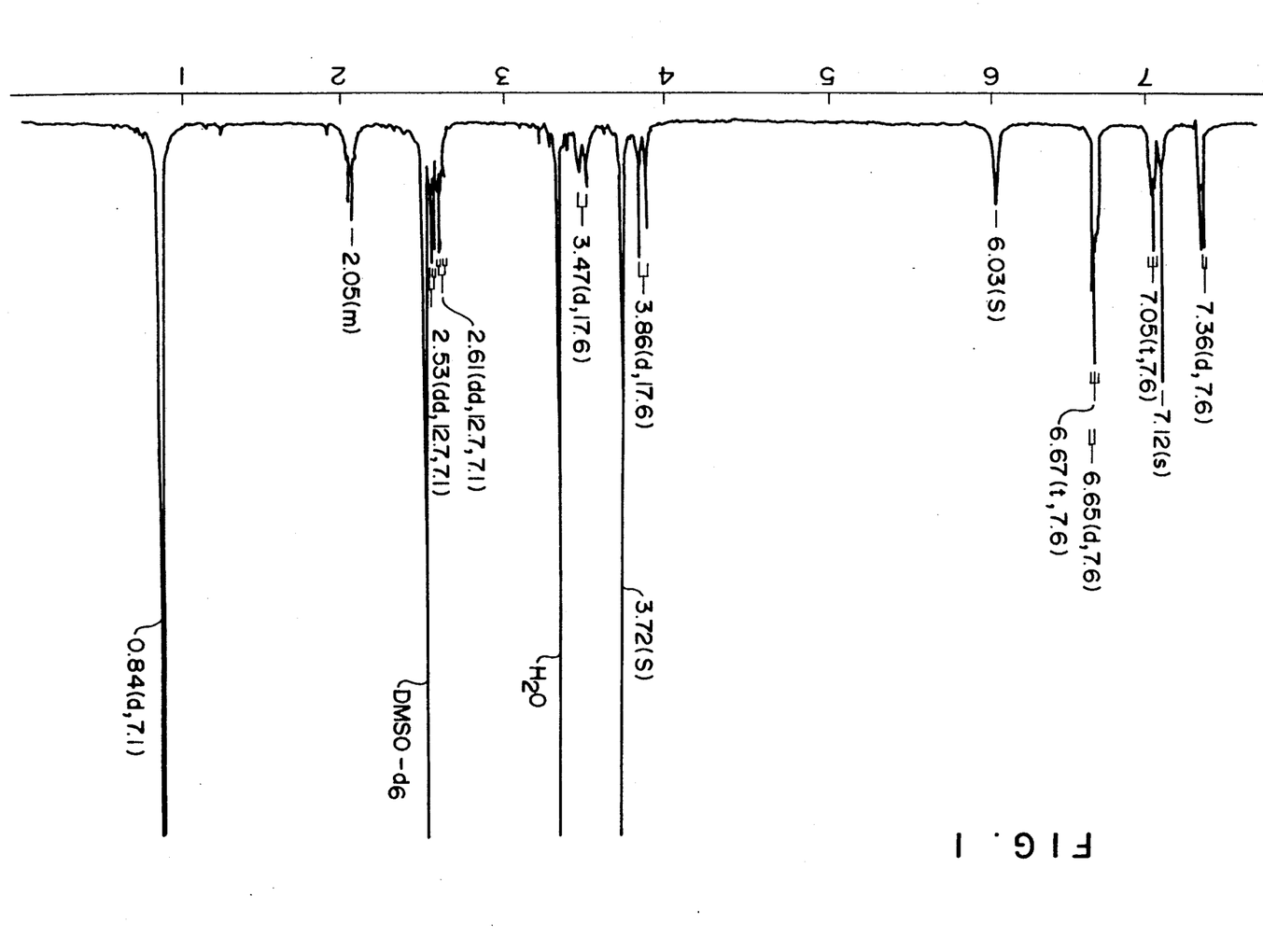
FIG. 1 shows $^1$H-NMR spectrum chart of a novel intermediate compound of NF-1616-902 of the present invention.

(9) Nuclear magnetic resonance spectrum ($^1$H-NMR):
Determined in DMSO-$D_6$ at 400 MHz.
Results are shown in the attached FIG. 1.
$\delta = 7.36$ (d, J=7.6, 2H)
7.12 (s, 2H)
7.05 (t, J=7.6, 2H)
6.67 (t, J=7.6, 2H)
6.65 (d, J=7.6, 2H)
6.03 (s, 2H)
3.86 (d, J=17.6, 2H)
3.72 (s, 6H)
3.47 (d, J-17.6, 2H)
2.61 (dd, J=12.7 and 7.1, 2H)
2.53 (dd, J=12.7 and 7.1, 2H)
2.05 (m, 2H)
0.84 (d, J=7.1, 12H).

(10) Nuclear magnetic resonance spectrum ($^{13}$C-NMR)

Figure 2:
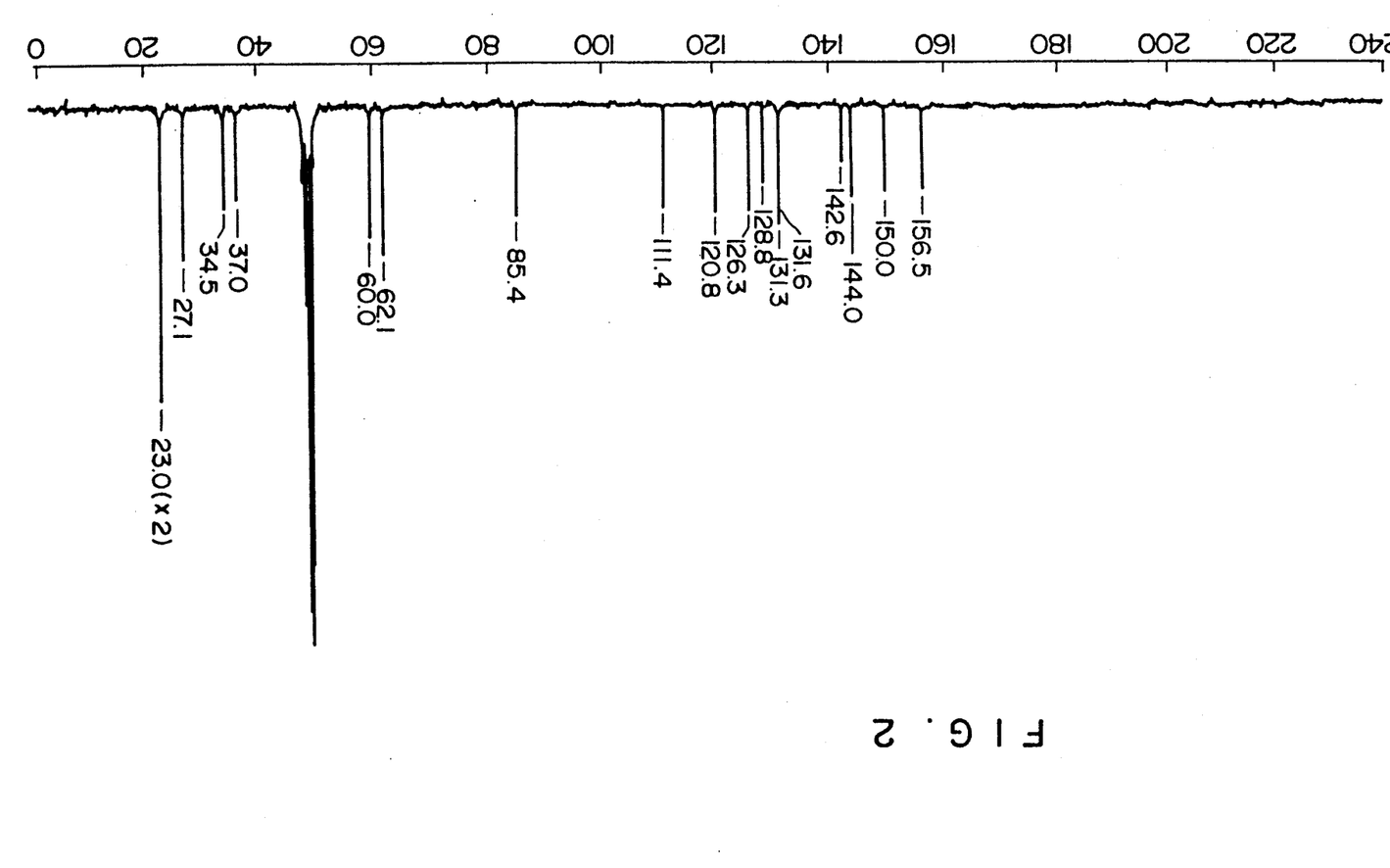
FIG. 2 shows $^{13}$C-NMR spectrum chart of the same intermediate compound.

Determined in $CD_3OD$ at 50 MHz, the results of −C-NMR are shown in the attached FIG. 2. Most of the peaks in the chart are as follows.

$\delta = 156.5$, 150.0, 144.0, 142.6, 131.6, 131.3, 128.8, 126.3, 120.8, 111.4, 85.4, 62.1, 60.0, 37.0, 34.5, 27.1, 23.0.

Figure 3:
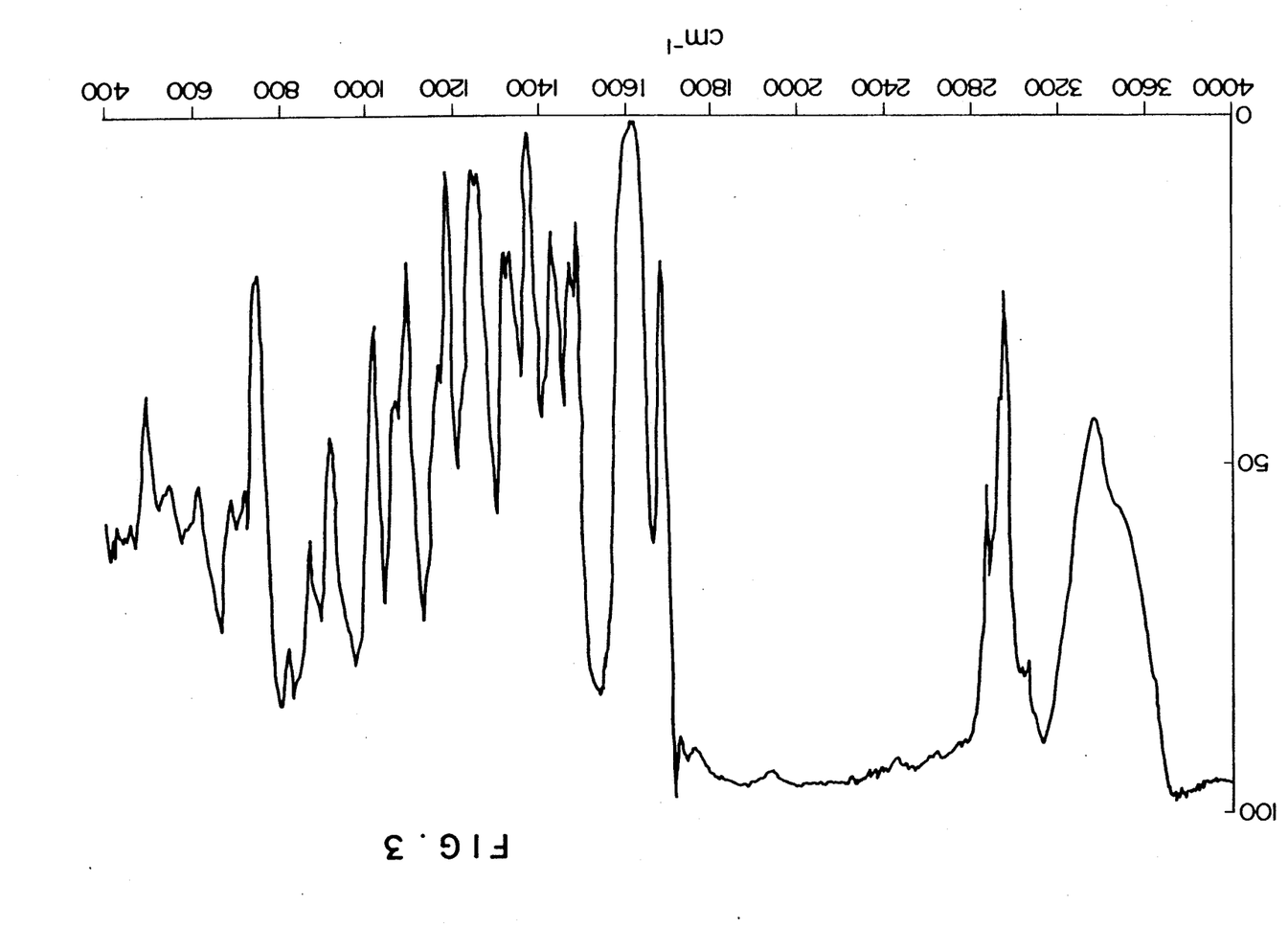
FIG. 3 shows IR-absorption spectrum chart of the same intermediate compound.

(11) Infrared absorption spectrum (IR):

IR absorption spectrum chart by using KBr method is shown in the attached FIG. 3 in which major absorption bands are as follows. 352, 2950, 2852, 1680, 1610, 1480, 1425, 1371, 1330, 1315, 1255, 1240, 1182, 1092, 1018, 750 cm$^{-1}$.

Pharmacological Test-1

Effect for decreasing the tolerance against Vincristine in P388/VCR cells

This test was conducted by the procedures similar to those described in an article by T. Tsuruo, et al. in Cancer Research, Vol. 44, (1984), pages 5095–5099.

First, P388/VCR cells were suspended in the concentration of $5 \times 10^4$ cells/ml in a culture medium of RPMI-1640 + 10% fetal calf serum (FCS) + 10 μm 2-mercaptoethanol. Next, a solution prepared by dissolving the intermediate compound of NF-1616-902 in dimethyl sulfoxide (DMSO) was provided, then the predetermined amount of this solution was added to the above-mentioned suspension of P388/VCR cells.

Similarly, Vincristine was added to the above-mentioned suspension of the cells by making serial twofold dilutions, and each of the suspensions of the cells was incubated in an incubator in which 5% of $CO_2$ + 95% air was filled for 48 hours. Survival rate of the cells were determined and the concentrations of the compound of NF-1616-902 for decreasing the tolerance of the cells against Vincristine were obtained.

The results of test is shown the following Table 1.

TABLE 1

| | Concentration of compound NF-1616-902 (μm/ml) | Cytotoxic concentration of Vincristine (ng/ml) |
| --- | --- | --- |
| Control group | 0 | 100 |
| Test group | 10 | 1 |
| Test group | 5 | 4 |
| Test group | 2.5 | 20 |

As can be seen from the data shown in Table 1, the intermediate compound of NF-1616-902 possesses the effect for decreasing the tolerance of cancer cells against Vincristine when it is used jointly with Vincristine. Generally, acquirement of the tolerance of cancer cells against an anti-tumor agents is one of the most important problems in conducting cancer therapies. As shown in the above, the intermediate compound of NF-1616-902 of the present invention is useful agent in conducting cancer therapies, for the reason that when the intermediate compound of NF-1616-902 is used jointly with an anti-tumor agent (in this case, Vincristine), the effect for decreasing the tolerance of the cancer cells against said anti-tumor agent can be expected. In addition to the above, it is confirmed that said effect of the intermediate compound of NF-1616-902 is not limited only to the use jointly with Vincristine, but also effective when it is used jointly with other anti-tumor agents, for example, Daunomycin, Vinblastine, Mitomycin, Bleomycin, and the like.

EXAMPLE 2

Preparation of the desired pyrazinoxide compound of NF-1616-904 of the present invention The intermediate compound of NF-1616-902 obtained in Example 1 was dissolved in methanol, and 2 N-NaOH solution was added thereto in the ratio of 2:1 (volume by volume), then the mixture was allowed to stand at room temperature for 48 hours. Then this mixture was neutralized with 6 N-HCl, and extracted with ethyl acetate, the extract was subjected to a column chromatography by using Sephadex LH-20 column and eluted with a solvent of chloroform:methanol (2:1) to yield the desired pyrazinoxide compound of NF-1616-904, then crystallized from methanol. Thus obtained pyrazinoxide compound of NF-1616-904 was subjected to structural analysis by means of X-ray crystallography. The following crystallographycal data were obtained.

Crystallographycal data for $C_{18}H_{21}N_3O_3$
Triclinic, space group $$P1, \quad a = 10.804\ (4),$$
$$b = 12.7986\ (5),$$
$$c = 13.564\ (6)\ \text{Å},$$
$$\alpha = 86.07\ (3),$$
$$\beta = 107.00\ (3),$$
$$\gamma = 106.93\ (3),$$
$$z = 4$$

As the result of the structural determination conducted by direct method of MULTAN program, the chemical structural formula of the pyrazinoxide compound of NF-1616-904 was confirmed as shown in the formula (1) indicated previously.

Physico-chemical properties of the desired pyrazinoxide compound of NF-1616-904 are as follows:

(1) Appearance: Yellow crystals (recrystallized from methanol)
(2) Melting point: 223.5°–225.5° C.
(3) Mass spectrum (EI): $M^{\oplus} = 327$, 311, 310, 268, 193,
(4) Ultraviolet absorption spectrum (Ethanol):

$$\lambda max\ (E^{1\%}_{1\ cm}) = 354\ (233, \epsilon = 7370)$$
$$287\ (sholder)$$
$$279\ (326, \epsilon = 10320)$$
$$273\ (sholder)$$
$$220\ (1558, \epsilon = 49390)$$

(5) Nuclear magnetic resonance spectrum ($^1$H-NMR):

Determined in DMSO-$d_6$ at 250 MHz.
Results of $^1$H-NMR are shown as follows:
$\delta = 11.96$ (bs, 1H)
10.97 (s, 1H)
7.59 (d, J=7.8, 1H)
7.36 (d, J=7.9, 1H)
7.27 (d, J=2.1, 1H)
7.08 (dt, J=1.3 and 7.8, 1H)
6.99 (dt, J=1.3 and 7.8, 1H)
3.93 (s, 2H)
3.78 (s, 3H)
2.62 (d, J=7.2, 2H)
2.11 (m, 1H)
0.86 (d, J=6.7, 6H).

(6) Nuclear magnetic resonance spectrum ($^{13}$C-NMR):

Determined in CDCl$_3$-CD$_3$OD at 62 MHz.
Results of $^{13}$C-NMR are shown as follows:
$\delta = 157.82$, 143.88, 142.24, 137.20, 131.06, 127.21, 124.27, 122.42, 119.60, 118.72, 112.09, 109.36, 62.08, 33.99, 26.53, 24.60, 23.04.

(7) Infrared absorption spectrum (IR):

The following absorption bands were observed as the results of IR absorption spectrum by using KBr method.
3250, 2950, 2910, 1620, 1450, 1409, 1370, 1330, 1241, 1090, 990, 735 cm$^{-1}$.

Pharmacological Test-2

Inhibitory effect of the pyrazinoxide compound of NF-1616-904 against superoxide radicals ($O_2^-$) release from the peritoneal macrophage cells of guinea pig by stimulation:

Mineral oil was intraperitoneally administered to a guinea pig, then 96 hours after the administration, the peritoneal microphage cells were obtained.

Superoxide radicals ($O_2^-$) were determined by means of reduction of cytochrome C according to the procedures described in an article by T. Matsumoto, et al. in Biochemical and Biophysical Research Communications, Vol. 88, No. 3 (1979), pages 974–979.

Thus, the peritoneal macrophage cells were added to make the final concentration of $2 \times 10^6$ cells/ml into 1 ml of 80 $\mu$M-cytochrome C solution, further the pyrazinoxide compound of NF-1616-904 was added thereto to make the test group sample. On the other hand, water added in place of the pyrazinoxide compound of NF-1616-904 to make the control group sample. Both test group and control group samples were subjected to a pure incubation at 37° C. for 1 minute.

As to the stimulating agent for releasing superoxide radicals ($O_2^-$), formylmethionylleucylphenylalanine (FMLP) was added to make the final concentration of $10^{-7}$M into the above-mentioned test group sample and control group sample. Then, both samples were subjected to additional reaction for 1 minute.

Difference of the absorbances measured at 550 nm (OD$_{550}$) of both test group and control group samples were determined, and the 50% inhibitory concentration (IC$_{50}$) was obtained by calculating as the ratio of OD$_{550}$ of the test group sample to that of the control group sample. The IC$_{50}$ value obtained was $1.2 \times 10^{-5}$.

Pharmacological Test-3

Anti-albuminuria activity of the pyrazinoxide compound of NF-1616-904 in *Masugi nephritis*

Rat nephrotoxin (hereinafter referred to as "NT") was prepared as follows. Thus, the kidney cortex of a rat was homogenized with an equal amount of physiological saline, then the thus obtained homogenate was admixed with Freund's complete adjuvant (manufacture by Difco Laboratories, Inc., Detroit, Mich., U.S.A.) in the ratio of 1:1. Then, 2 ml of this mixture was administered subcutaneously to a rabbit (body weight: 3.1 kg) to have said rabbit immunized. 1.5 Months after the immunization, the blood was sampled from the heart of said rabbit, and the serum was obtained therefrom. The serum thus obtained was inactivated at 56° C. for 30 minutes, and subjected to fractionation by salting out with a aqueous solution saturated with 40% of ammonium sulfate. By sampling of immunoglobulin-γ-globulin (IgG) fraction, the desired NT was obtained.

This test was conducted by using Wisterstrain male rats having 150–160 g body weight. Pyrazinoxide compound of NF-1616-904 of the present invention simultaneously with NT were orally administered forcedly. Additionally, 1 ml of NT was administered intravenously to the tail vein of said rat. On the other hand, in place of pyrazinoxide compound of NF-1616-904, physiological saline was administered to other rats to make the control group.

The total amount of urinary protein being excreted in the urine during 24 hours after the administration of NT was determined by turbidity method using sulfosalicylic acid and bovine serum albumin (BSA) as the reference substance, according to procedures described in an article by F. Kingsbury, et al. in J. Lab. Clin. Med., Vol. 11, (1926), pages 981–989.

The ratio of inhibition of albuminuria (%) in the test group was calculated by referring to the measured value in the control group. The test results are shown in the following Table 2, in which each of the test data are shown at the mean value±S. E. of the six rats used in each of test and control groups.

TABLE 2

| Dosage of pyrazinoxide compound of NF-1616-904 (mg/kg) | Albuminuria (mg/day) | Ratio of inhibition of albuminuria (%) |
| --- | --- | --- |
| Control group (Six rats) 0 mg/kg | 120 ± 30 | — |
| Test group (Six rats) | | |
| 60 mg/kg | 88 ± 18 | 26.7 |
| 30 mg/kg | 45 ± 16 | 62.5 |

As can be seen from the test data obtained in Pharmacological Test-2 and -3, the pyrazinoxide compound of NF-1616-904 possesses clearly inhibitory effect against super-oxide radicals as well as possesses anti-albuminuria activity in nephritis. Thus, the pyrazinoxide compound of NF-1616-904 according to the present invention is useful agent for preventing and treating not only nephritis but also various diseases caused by super-oxide radicals, for example autoimmune diseases such as rheumatoid arthritis, arteriosclerosis, ischemic heart disease, transient cerebral ischematic attack, hepatic insuffiency, renal insufficiency and the like.

Example of pharmaceutical preparation

A pharmaceutical composition containing pyrazinoxide compound of NF-1616-904 as the active ingredient were prepared with the following formulation.

| | |
| --- | --- |
| Pyrazinoxide compound of NF-1616-904 of the present invention | 150.0 g |
| Citric acid | 1.0 g |
| Lactose | 33.5 g |
| Dicalcium phosphate | 70.0 g |
| Pluronic F-68 (Trademark for a series of poloxyalkylene derivatives of propylene glycol, manufactured by BASF-Wyandott Corp., N.J., U.S.A.) | 30.0 g |
| Sodium laurylsulfate | 15.0 g |
| Polyvinylpyrrolidone | 15.0 g |
| Carbowax 1500 (Trademark for a series of polyethylene glycols, manufactured by Union Carbide Corp., N.Y., U.S.A.) | 4.5 g |
| Carbowax 6000 | 45.0 g |
| Corn starch | 30.0 g |
| Dried sodium laurylsulfate | 3.0 g |
| Dried magnesium stearate | 3.0 g |
| Ethanol q.s. | |

Pyrazinoxide compound of NF-1616-904 of the present invention, citric acid, lactose, dicalcium phosphate, Pluronic F-68 and sodium laurylsulfate were admixed together thoroughly to obtain a mixture. The mixture thus obtained was sieved through a screen of No. 60, then such sieved powder of mixture was subjected to wet-granulation with an ethanol solution containing polyvinylpyrrolidone, Carbowax 1500 and Carbowax 6000. The powder of mixture was shaped into a paste-like lump by adding an adequate amount of ethanol, if necessary. Corn starch was added to this lump and well kneaded to form the lump into granules having uniform particle size. The granules thus obtained were sieved through a screen of No. 10, then the sieved granules were placed on a tray and dried in an oven at 100° C. for 12–14 hours. The dried granules were sieved through a screen of No. 16, and were added thereto dried sodium laurylsulfate and dried magnesium stearate, then the whole mixture was mixed well and was compressed into the desired form by using a tablet machine to obtain tablets to be used for the core portions of coated tablets. The core portions were treated with a varnish, and further the treated surface thereof were coated with talc for preventing the surface from the adsorption of moisture. The treated surface of core portions were further coated with a primary coating layer, and further coated with a varnish to make a sufficient number of layers for preparing coated tablets for oral administration. In order to make the coated core portions of tablets into complete spherical form and to make the treated surface smoothly, the coated tablets were further coated with primary coating layers and smoothing coating layers. The coated tablets were color coated until the desired color of the surface was obtained. After the coated tablets were dried, the surface thereof were polished to make them uniform gloss.

What is claimed is:

1. Pyrazinoxide compound of NF-1616-904 having the formula (1),

2. A pharmaceutical composition for preventing and treating diseases caused by superoxide radicals containing, as the active ingredient, a therapeutically effective amount of a pyrazinoxide compound of NP-1616-904 having the formula (1) as claimed in claim 1 and a pharmaceutically acceptable carrier, wherein said diseases are selected from the group consisting of rheumatoid arthritis, arteriosclerosis, ischemic heart disease, transient cerebral ischemic attack, hepatic insufficiency, renal insufficiency and nephritis.

3. A pharmaceutical composition for preventing and treating nephritis containing, as the active ingredient, a therapeutically effective amount of a pyrazinoxide compound of NF-1616-904 having the formula (I) as claimed in claim 1 and a pharmaceutically acceptable carrier.

4. A pharmaceutical composition for preventing and treating autoimmune diseases containing, as the active ingredient, a therapeutically effective amount of pyrazinoxide compound of NF-1616-904 having the formula (I) as claimed in claim 1 and a pharmaceutically acceptable carrier.

5. A pharmaceutical composition for preventing and treating renal insufficiency containing, as the active ingredient, a therapeutically effective amount of a pyrazinoxide compound of NF-1616-904 having the formula (I) as claimed in claim 1 and a pharmaceutically acceptable carrier.

6. The pharmaceutical composition according to claim 4, wherein the autoimmune disease is rheumatoid arthritis.

7. The pharmaceutical composition according to claim 2, wherein the disease caused by superoxide radicals is ischematic heart disease.

8. The pharmaceutical composition according to claim 2, wherein the disease caused by superoxide radicals is transient cerebral ischematic attack.

* * * * *